United States Patent
Fix et al.

(10) Patent No.: US 8,237,204 B2
(45) Date of Patent: Aug. 7, 2012

(54) METHOD FOR PASSIVATING A FIELD-EFFECT TRANSISTOR

(75) Inventors: Richard Fix, Gerlingen (DE); Oliver Wolst, Nuertingen (DE); Stefan Henneck, Leonberg (DE); Alexander Martin, Ludwigsburg (DE); Martin Le-Huu, Korntal (DE)

(73) Assignee: Robert Bosch GmbH, Stuttgart (DE)

( * ) Notice: Subject to any disclaimer, the term of this patent is extended or adjusted under 35 U.S.C. 154(b) by 102 days.

(21) Appl. No.: 12/619,304

(22) Filed: Nov. 16, 2009

(65) Prior Publication Data
US 2010/0133591 A1 Jun. 3, 2010

(30) Foreign Application Priority Data
Nov. 19, 2008 (DE) .......................... 10 2008 043 858

(51) Int. Cl.
*G01N 27/403* (2006.01)
(52) U.S. Cl. ................ 257/253; 257/414; 257/E21.294; 204/403; 204/416
(58) Field of Classification Search ................... 257/253, 257/414, E21.294; 204/403, 416
See application file for complete search history.

(56) References Cited

U.S. PATENT DOCUMENTS

| 4,874,499 A * | 10/1989 | Smith et al. ............. 204/403.03 |
|---|---|---|
| 5,698,771 A | 12/1997 | Shields et al. |
| 6,111,280 A | 8/2000 | Gardner et al. |
| 6,221,673 B1 | 4/2001 | Snow et al. |
| 6,703,241 B1 | 3/2004 | Sunshine et al. |
| 2005/0062093 A1* | 3/2005 | Sawada et al. ................. 257/316 |
| 2005/0230271 A1* | 10/2005 | Levon et al. ................... 205/789 |
| 2007/0009744 A1 | 1/2007 | Besinger et al. |
| 2008/0010707 A1 | 1/2008 | Zhang et al. |

FOREIGN PATENT DOCUMENTS
DE 112005000250 2/2007
* cited by examiner

*Primary Examiner* — Tan N Tran
(74) *Attorney, Agent, or Firm* — Kenyon & Kenyon LLP

(57) ABSTRACT

The present invention relates to a method for passivating a semiconductor component having at least one chemosensitive electrode that is blinded by the application of a glass layer. The present invention also relates to a device for detecting at least one substance included in a fluid stream, including at least one semiconductor component acting as a measuring sensor as well as at least one semiconductor component acting as a reference element, the semiconductor components each having a chemosensitive electrode, and the chemosensitive electrode of the semiconductor component acting as the reference element being passivated. For the passivation, a glass layer may be applied at least to the chemosensitive electrode of the semiconductor component acting as reference element.

4 Claims, 1 Drawing Sheet

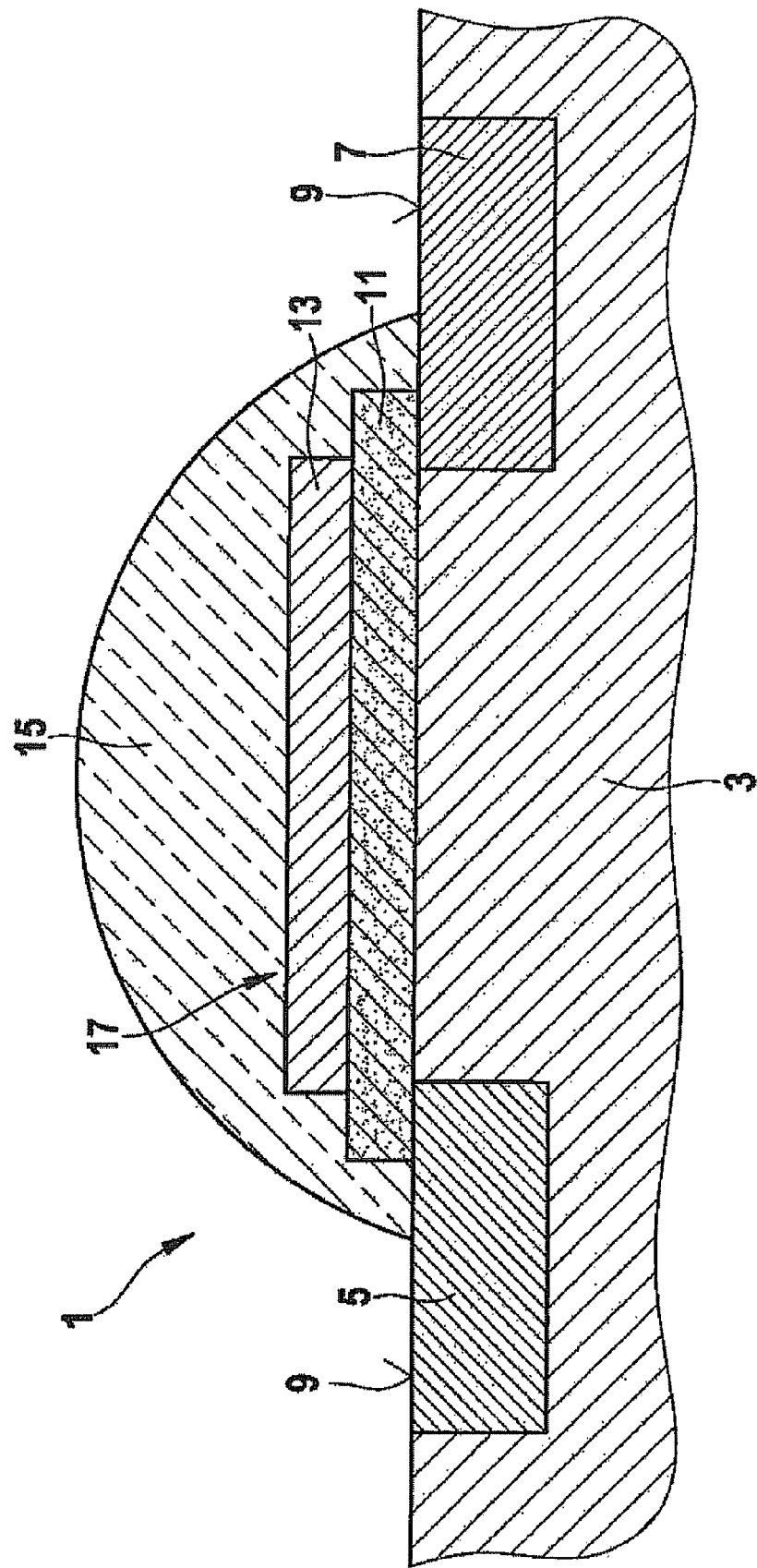

METHOD FOR PASSIVATING A FIELD-EFFECT TRANSISTOR

FIELD OF THE INVENTION

The present invention relates to a method for passivating a field-effect transistor having at least one source electrode, one drain electrode and one gate electrode. The present invention also relates to a device for detecting at least one substance contained in a fluid stream.

BACKGROUND INFORMATION

Gas-sensitive field-effect transistors based on semiconductors are increasingly being used in sensor systems. The application of a test species that is to be detected, in this context, for instance, a gas or a liquid, or a gas/liquid mixture, usually leads to a change in the channel impedance, and thus to a change in the current flowing from the source electrode to the drain electrode through the transistor. Such a field-effect transistor is known, for instance, from U.S. Pat. No. 5,698,771. The use of field-effect transistors is possible at up to 800° C. in sensor system applications, if semiconductor substances having a band gap of more than 2 eV, such as gallium nitride or silicon carbide, are used.

At the working point selected, the channel current of the field-effect transistor is frequently greater by some orders of magnitude (usually 103) than the change in the channel current because of the application of the test species. From this there comes about a great requirement for current measurement. In addition, a problem arises that the offset is able to be influenced by external interferences, so-called noise. Such external interference influences are, for instance, temperature changes or sensor degradation, which lead to changes in the channel current, and are not based on the presence of test species. Based on the given signal-offset ratio, the change in the channel current by interference influences may be of the same order of magnitude, or even greater in the least favorable case, than the change that takes place owing to the presence of test species. Since one cannot exclude these interference influences completely, the error in the measuring signal connected therewith may be large, and may prevent a usable measurement of the test species, in the least favorable case.

In order to compensate for interference influences and offsets, it is possible, for example, to use a field-effect transistor acting as a reference element, which is insensitive with respect to the substances to be detected. The reference element is preferably identical to the field-effect transistor acting as the measuring sensor with regard to its semiconductor patterns, geometric dimensions and electrical characteristics. Both field-effect transistors have the same zero signal, because of the same electrical characteristics. When the two field-effect transistors are slightly separated spatially, there also exists good heat coupling. This is a given, for instance, in response to the integration of the components on a chip. Because of this, the two field-effect transistors experience the same interference influences. A difference in the channel current of the field-effect transistor acting as measuring sensor may then be attributed only to the presence of the substances that are to be detected.

The passivating of field-effect transistors so as to make them into reference elements is accomplished according to the related art in a semiconductor process, with the aid of dielectric layers. These are generally deposited using thin-film techniques. However, such a passivating layer may, under certain circumstances, influence the electrical characteristics of the field-effect transistor. Thus, for example, stresses at the boundary layer between the passivating layer and the layer below it, in the case of piezoelectric semiconductor substances, such as gallium nitride, may lead to a change in the field-effect transistor channel. In addition, dielectric passivating layers frequently have electron states which are able to store loads, and are therefore able to influence the electric field under the gate electrode.

In addition, the passivating of a field-effect transistor used as a reference element on an integrated chip is very costly. Thus, process technology restrictions do not permit complete lateral patterning of the passivation, for example, and, on the other hand, for example, process parameters, such as high temperatures during the depositing of the passivation, damage the chemically sensitive gate of the measuring sensor. For this reason, field-effect transistors acting as a reference element and field-effect transistors acting as a measuring sensor have to be processed separately from one another. Under certain circumstances, this may lead to the field-effect transistors no longer being identical, possibly having different electrical characteristics.

SUMMARY OF THE INVENTION

In an example method of the present invention for passivating a semiconductor component having at least one chemosensitive electrode, at least the chemosensitive electrode is blinded by the application of a glass layer or a glass-ceramic layer. The glass layer or glass-ceramic layer may be present in an amorphous, partially crystalline or crystalline state.

Because of the application of the glass layer or the glass-ceramic layer, the chemosensitive electrode of the semiconductor component becomes insensitive to substances that are to be detected, and thus prevent substances present in the fluid stream from interacting with the chemosensitive electrode of the semiconductor component. Such semiconductor components may be used particularly as reference elements for eliminating interference influences in devices for detecting substances in a fluid stream.

An advantage of applying a glass layer or a glass-ceramic layer to the chemosensitive electrode is that the semiconductor component acting as a reference element may have an identical construction with respect to the semiconductor patterning, the geometric dimensions, the construction of the gate stack as well as the electrical characteristics as the semiconductor component used as the measuring sensor. Because of the identical construction, differences in the channel current of the semiconductor component acting as the measuring sensor and the semiconductor component acting as the reference element, may now be attributed only to the presence of substances that are to be detected. In this case, measuring does not take place with the aid of a current change of a single semiconductor component, but with the aid of the difference of the channel current between the semiconductor component acting as the measuring sensor and the semiconductor component acting as the reference element.

In an example embodiment of the present invention, the application of the glass layer or the glass-ceramic layer to at least the chemosensitive electrode of the semiconductor component, for the purpose of blinding it, i.e., to make the chemosensitive electrode insensitive to the influence of substances in a fluid stream, takes place, for example, by applying a suspension containing glass powder dispersed in a solvent to the chemosensitive electrode. The solvent is subsequently evaporated and the glass powder is melted. Additional components, that are perhaps contained in the suspension, and that do not evaporate, are burned off by the high temperatures required to melt the glass. In this way, a glass film remains on the chemosensitive electrode of the semiconductor component which is free of organic occlusions. The glass powder preferably includes glass that melts at a temperature in the range of 400 to 800° C. The melting temperature is, however, above the later operating temperature of the semiconductor component, so as to avoid having the glass layer melt again during the operation of the semiconductor component. The softening temperature of the glass is preferably more than 50° C. higher than the operating temperature of the semiconductor component. In order not to damage the substances of the semiconductor component or rather the semiconductor component during the melting of the glass, it is preferred that one select a glass having as low a melting temperature as possible.

The melting of the glass preferably takes place at a heating rate of up to 100 K/s, a holding time in the range of 0 to 60 minutes and a cooling rate of up to 50 K/s.

The glass powder or the glass-ceramic powder, used to form the glass layer or the glass-ceramic layer, is either free of alkali or contains alkali. One advantageous alkali-free glass powder is silicate glass powder, for example, that contains bismuth, zinc, boron or combinations of these substances, for example, bismuth-boron-zinc silicate glass powder. The advantage of a bismuth-boron-zinc-silicate glass powder is that it already melts at a temperature of approximately 600° C. Alkali and/or alkaline earth-containing glass powder or glass-ceramic powder may be used, for instance, alkali-alkaline earth-boron silicate glass powder.

Glasses which melt at low temperatures, that is, at temperatures of approximately 600° C., generally almost always contain high proportions of lead oxide or bismuth oxide. Because of the high proportion of lead oxide or bismuth oxide, the glasses are generally more easily reducible than high-melting point glasses rich in silicon oxide. The reduction of the glass takes place, for example, in the presence of carbon monoxide or in response to a reaction with the surface of the semiconductor chip. Since the reduction leads to damage to the glass layer, glasses that contain only a slight proportion of lead oxide or bismuth oxide are preferably used.

Also available are alkali-alkaline earth boron silicate glasses that melt at low temperatures, but they generally have high thermal coefficients of expansion. The thermal coefficient of expansion of the alkali-alkaline earth boron silicate glass powder is generally higher than the thermal coefficient of expansion of the silicon carbide used for the semiconductor component as semiconductor material. However, the thermal coefficient of expansion may be adjusted by the addition of an additive having a thermal coefficient of expansion that is lower than the thermal coefficient of expansion of the alkali-alkaline earth boron silicate glass, for example. Suitable additives are cordierite or lithium-aluminum silicate glass ceramics, for instance. Because of this additive, a glass-ceramic composite is formed by melting and subsequent solidification.

In an example embodiment of the present invention, in order for the glass not to form cracks if there is a deviation in the thermal coefficient of expansion of the semiconductor material and the glass, it is preferred to form the glass so as to have a small layer thickness. However, in an example embodiment, the layer thickness is big enough so that the glass is sealed from the fluid stream. The layer thickness is therefore preferably in a range of 0.1 to 100 μm, and further preferably in a range of 1 to 50 μm.

The solvent in which the glass powder is dispersed may be an ester or an alcohol ketone.

Beside the solvent, the suspension may also contain a binding agent. Suitable binding agents are polymethacrylate or cellulose nitrate, for example.

Greater viscosity of the suspension may be achieved by using the binding agent. In this way, it is possible, for example, for the suspension to be in the form of a paste. This avoids having the suspension run off the semiconductor component after being applied, and thus taking up an undefined shape, and possibly even covering areas on the semiconductor component that should not be covered by the glass layer.

The application of the suspension may be made by any suitable printing method, by dispensing it on or by pico-deposition methods. Screen printing or dropping it on are suitable methods for applying the suspension, for example.

According to an example embodiment, the chemosensitive electrode, which is blinded by the application of the glass layer, is preferably a gate electrode of a field-effect transistor or a diode.

Example embodiments of the present invention also relate to a device for detecting at least one substance contained in a fluid stream. The device may include at least one semiconductor component acting as a measuring sensor and at least one semiconductor component acting as a reference element, the semiconductor components each having a chemosensitive electrode. In an example embodiment, the chemosensitive electrode of the semiconductor component acting as a reference element is passivated. In an example embodiment, a glass layer is applied at least to the chemosensitive electrode of the semiconductor component acting as reference element, for the passivation.

Because of the glass layer, interaction of components of a fluid with the semiconductor component, which may thus lead to a measuring signal, as was described above, may be avoided. The semiconductor component, acting as reference element, may be used so as to be able to eliminate interference influences which might act upon the detection device.

In one preferred specific example embodiment, the semiconductor component acting as reference element and the semiconductor component acting as measuring sensor are developed as an integrated component on a chip. In a particularly preferred example embodiment, the semiconductor component acting as reference element and the semiconductor component acting as measuring sensor have a matching design. Because of the matching design, particularly with respect to the semiconductor patterning, the geometric dimensions, the construction of the gate stack, and the electrical characteristics, both the semiconductor component acting as measuring sensor and the semiconductor component acting as reference element react in the same way to environmental influences, such as fluctuations in the temperature. These interference influences may be eliminated, in an example embodiment of the present invention, by subtraction of the signals of the semiconductor component acting as measuring sensor and the semiconductor component acting as reference element.

Besides a matching design of the semiconductor component acting as reference element and the semiconductor component acting as measuring sensor, it is alternatively possible according to an example embodiment of the present invention, however, to functionalize only the semiconductor components acting as measuring sensor, for example, but to apply to the semiconductor components acting as reference elements a deviating metallization of the gate electrode, already in the semiconductor process.

Particularly when the designs of the semiconductor component acting as measuring sensor and the semiconductor component acting as reference element have essentially matching designs, it is possible first to produce the two semiconductor components and, only after the production of the semiconductor components, to passivate the chemosensitive electrode of the semiconductor component acting as reference element by applying the glass layer according to the present invention. For the passivation, an example embodiment of the present invention may require that the glass layer cover, in a gas-tight manner, at least the chemosensitive electrode of the semiconductor component acting as reference element. One may also cover a greater area than the area of the chemosensitive electrode, however. Thus, it is possible, for example, to cover the entire semiconductor component acting as reference element, or even more than the semiconductor component acting as reference element, using the glass layer. If both the semiconductor component acting as measuring sensor and the semiconductor component acting as reference element are processed on a common chip, it should be ensured that the chemosensitive electrode of the semiconductor component acting as measuring sensor does not become covered by the glass layer.

In an example embodiment of the present invention, the semiconductor component acting as measuring sensor or the semiconductor component acting as reference element is preferably a field-effect transistor or a diode. In the case of gases to be detected, a gas-sensitive field-effect transistor or a gas-sensitive diode may be involved.

BRIEF DESCRIPTION OF THE DRAWINGS

The drawings illustrate generally, by way of example, but not by way of limitation, an example embodiment of the present invention discussed in detail in the following description.

FIG. 1 shows a schematic representation of a cross section through a semiconductor component developed according to an example method of the present invention.

DETAILED DESCRIPTION

According to an example embodiment of the present invention, a semiconductor component 1 generally includes a substrate 3 made of a semiconductor material. In principle, all semiconductor substances that have a bandwidth of more than 2 eV are suitable as the semiconductor material. For example, silicon carbide or gallium nitride are suitable semiconductor substances. ZnO or diamond, for instance, are other suitable semiconductor substances.

In an example embodiment of the present invention, where the semiconductor component 1 is a field-effect transistor, it includes at least one source electrode 5 and one drain electrode 7. In an example embodiment, source electrode 5 and drain electrode 7 are enclosed by semiconductor material 3 and have one free surface 9. Alternatively, however, it is also possible that source electrode 5 and drain electrode 7 are applied onto semiconductor material 3.

Platinum, titanium, tantalum, silicides or carbides are suitable as the material for source electrode 5 and drain electrode 7.

In the illustrated example embodiment, free surfaces 9 of source electrode 5 and drain electrode 7 and the surface of substrate 3 form an even surface. Shown to be applied to this surface is a dielectric 11 that partially covers source electrode 5, drain electrode 7, and substrate 3 lying between the source electrode and drain electrode 7. Suitable materials for dielectric 11 are oxides such as $SiO_2$, $Al_2O_3$, $ZrO_2$, nitrides such as $Si_3N_4$ or carbides such as SiC.

An electrically conductive layer 13 is shown to be applied to dielectric 11. In an example embodiment of the present invention, in the case of a field-effect transistor, electrically conductive layer 13 is a gate electrode 17.

Besides the illustrated two-layer construction, made up of dielectric 11 and electrically conductive layer 13, a design using more than two layers is also possible. Thus, an additional layer made of a dielectric substance and an additional electrically conductive layer may be applied, for example. Furthermore, it is also possible to apply a porous layer, for example, which is catalytically active, and at which chemical reaction is able to take place. Alternatively, it is also possible that electrically conductive layer 13 is developed to be porous, for example. In addition, electrically conductive layer 13 may also contain catalytically active material, at which a chemical reaction can take place. Such a chemical reaction leads to a change in the gate voltage, whereby the presence of a substance, that is to be detected, is able to be determined.

Semiconductor component 1 used as reference element may additionally include a passivating layer on electrically conductive layer 13 that is used as gate electrode 17. The passivating layer may have a plurality of material layers, for instance. In general, however, no additional passivating layer is applied onto electrically conductive layer 13.

The application of dielectric 11, electrically conductive layer 13, and perhaps additional layers may take place by any method known to one skilled in the art and established in semiconductor technology. Suitable methods are, for instance, CVD methods or other micropatternable thin film methods such as vapor depositing and sputtering. If necessary, deposit baking steps may be added, which support a dense sintering of layers 11 and 13. Alternatively, however, it is also possible to provide a wet-chemical depositing of the material for dielectric substance 11, electrically conductive layer 13, and possibly additional layers, for example. A temperature treatment may be given following the wet-chemical depositing. The increased temperature of the temperature treatment results in the evaporation of the volatile solvents on the one hand, and dense sintering of the deposited material of layers 11 and 13 on the other hand. Alternatively, however, it is also possible, for instance, to apply dielectric 11 and electrically conductive layer 13 by a structuring thick layer method such as printing on using a paste, and perhaps a subsequent tempering step.

According to an example embodiment of the present invention, the passivation of gate electrode 17 formed by dielectric 11 and electrically conductive layer 13 takes place by applying a glass layer or the glass-ceramic layer 15. In an example embodiment, the glass of glass layer 15 is generally impervious to liquids or gases, so that these two do not reach electrically conductive layer 13. The application of the glass may be performed by a suitably appropriate method known to one skilled in the art. Thus, the glass for glass layer 15 may particularly be formed by applying a suspension or a paste of a glass powder by suitable printing methods, dispensing or pico-deposition methods. The paste or suspension of the glass powder applied is heated, so that the solvent contained in it evaporates. Subsequently, the paste or suspension is melted by heating at a suitable heating rate and holding time at suitable temperatures, and the organic components used to disperse the glass powder included in the suspension are burnt off. Thus it is possible, for instance, to apply a paste of an organic solvent, polymethacrylate and cellulose nitrate binder and a bismuth-boron-zinc silicate glass powder by screen printing or by dropping it on. According to an example embodiment, the paste is subsequently melted at a heating rate of up to 100 K/s, preferably of up to 50 K/s and a holding time in the range of 0 to 60 min, preferably of 5 to 15 min, at a temperature of 600° C. and a subsequent cooling at a cooling rate of up to 50 K/s. A glass layer 15 develops, which is gas-tight and essentially free of organic residues. The temperature of 600° C. is sufficient, in this context, to burn off the organic components that are contained in the suspension because of the polymethacrylate binder and the cellulose nitrate binder.

When selecting a suitable glass for glass layer 15, one should be careful that it has a sufficiently high melting point. Thus, it is preferred that the melting point of the glass be at least 50° C. higher than the temperature for the planned insertion of semiconductor component 1. On the other hand, one should also be careful that the temperature at which the glass, for glass layer 15, melts is not too high, so as to prevent degradation of semiconductor component 1 during the melting of the glass for glass layer 15.

Semiconductor component 1, having glass layer 15, is particularly suitable as reference element for the detection of gases in a gas stream. However, alternatively, for example, liquids in a liquid stream or gases dissolved in a liquid stream are also able to be detected. A semiconductor component 1 used as measuring sensor is additionally required for this, for the detection. In general, field-effect transistors or diodes are used as the semiconductor component 1.

Because of the construction, according to the present invention, using the glass layer or glass-ceramic layer 15 for semiconductor component 1 used as the reference element, it is possible to combine semiconductor components 1, that are essentially designed the same, as, respectively, a measuring sensor and as a reference element. According to an example method of the present invention, to produce this combination, the individual layers for the semiconductor component used as the measuring sensor and the semiconductor component used as the reference element are advantageously applied onto a substrate 3 at the same time. Because of this, one is able to achieve essentially the same layers with respect to their thickness and their design and their patterning. According to the example method, only subsequent to the processing of semiconductor component 1, i.e., when it is completely constructed, are the gate region of semiconductor component 1 that is used as the reference element (at least dielectric substance 11 and electrically conductive layer 13) covered by glass layer 15. It is also possible, however, to cover completely source electrode 5 and drain electrode 7 of the semiconductor component used as reference element using glass layer 15. A larger area of substrate 3 may also be covered by glass layer 15. Only the electrically conductive layer of gate electrode 17 of the semiconductor component used as the measuring sensor must not be covered by glass layer 15.

According to an alternative example embodiment of the present invention, it is also possible, in the case of semiconductor component 1 used as the reference element, to use substances for gate electrode 17 different from those of the semiconductor component 1 used as the measuring sensor. However, the design is preferably identical, so that interference signals lead to the same signal, both in the case of the semiconductor component 1 used as the measuring sensor and the semiconductor component 1 used as the reference element.

The simultaneous production of identical semiconductor components on one chip, of which only some, which are used as reference elements, are provided with glass layer 15, further has the advantage that they may be produced faster and more cost-effectively by the saving of numerous process steps.

Besides the field-effect transistor shown as semiconductor component 1 in FIG. 1, semiconductor component 1 that is passivated using glass layer 15, may also be any other semiconductor component that has a chemosensitive electrode, and is used for detecting gases. Thus, a chemosensitive electrode of a diode may also be provided with the glass layer, for example.

What is claimed is:

1. A device for detecting at least one substance included in a fluid stream, the device comprising:
    at least one semiconductor component acting as a measuring sensor and including a chemosensitive electrode; and
    at least one semiconductor component acting as a reference element and including a chemosensitive electrode passivated by a glass layer directly contacting and completely covering the chemosensitive electrode.

2. The device as recited in claim 1, wherein the semiconductor component acting as the reference element and the semiconductor component acting as the measuring sensor are developed as integrated components on a chip.

3. The device as recited in claim 1, wherein the semiconductor component acting as the reference element and the semiconductor component acting as the measuring sensor have a matching design.

4. The device as recited in claim 1, wherein at least one of the semiconductor component acting as the measuring sensor and the semiconductor component acting as the reference element is one of a field-effect transistor or a diode.

* * * * *